United States Patent [19]
Rebbe et al.

[11] 4,300,573
[45] Nov. 17, 1981

[54] SPHYGMOMANOMETER

[75] Inventors: Klaus Rebbe; Berd Rosicke; Klaus Wellmann, all of Mannheim, Fed. Rep. of Germany

[73] Assignee: Clinocon International GmbH, Mannheim, Fed. Rep. of Germany

[21] Appl. No.: 94,511

[22] Filed: Nov. 15, 1979

[30] Foreign Application Priority Data

Dec. 8, 1978 [DE] Fed. Rep. of Germany ....... 2853098

[51] Int. Cl.³ .............................................. A61B 5/02
[52] U.S. Cl. .................................. 128/686; 128/680; 128/327
[58] Field of Search .............................. 128/677–683, 128/686, 327

[56] References Cited

U.S. PATENT DOCUMENTS

| 2,753,863 | 7/1956 | Bailey | 128/686 X |
| 3,896,791 | 7/1975 | Ono | 128/686 X |
| 4,015,594 | 4/1977 | Siverson | 128/677 |
| 4,211,289 | 7/1980 | Klein | 128/686 |

FOREIGN PATENT DOCUMENTS

| 9789 | 4/1980 | European Pat. Off. | 128/686 |
| 42276 | 4/1933 | France | 128/686 |
| 1113204 | 11/1955 | France | 128/686 |
| 1535660 | 12/1978 | United Kingdom | 128/686 |

Primary Examiner—Kyle L. Howell
Attorney, Agent, or Firm—Sprung, Felfe, Horn, Lynch & Kramer

[57] ABSTRACT

Blood pressure measuring device having an inflatable cuff, a buckle and a sound pickup whose blood-pressure-related signals are either directly recognized and correlated with a pressure readout or processed by an electric circuit and delivered to at least one readout means giving the blood pressure values. The buckle forms one unit which houses the readout means and the electrical circuit for the conversation of the sound signals.

5 Claims, 2 Drawing Figures

SPHYGMOMANOMETER

BACKGROUND

This invention relates to a sphygmomanometer (blood pressure measuring device) having an inflatable cuff provided with a buckle, and a sound pickup whose signals relating to the blood pressure are either directly recognized and correlated with the pressure indication or are processed by an electrical circuit and delivered to at least one readout means showing the blood pressure values.

From German patent application No. 2,220,233 and U.S. Pat. No. 2,582,123 it is known to apply the measuring apparatus directly to the cuff. The advantage of the slightly more compact construction must be weighed against the disadvantage that, during a measurement, the measuring apparatus cannot be read by the person on whom the measurement is being performed.

SUMMARY

The invention provides a blood pressure measuring device of more compact construction, which is also easy to operate by one person and can be read by the same person.

This is achieved by making the buckle of the cuff one unit with the housing of the indicator means and the electrical circuit for the conversion of the sound signals.

Particularly advantageous and compact are sphygmomanometers of the invention in which a means for the manual pumping up of the cuff is permanently mounted in the direct vicinity of the cuff and the fastening buckle.

DESCRIPTION OF THE DRAWING

Additional advantageous developments are described in the subordinate claims and in the description that follows of embodiments diagrammatically represented in the drawing, wherein:

DESCRIPTION

Figure 1:
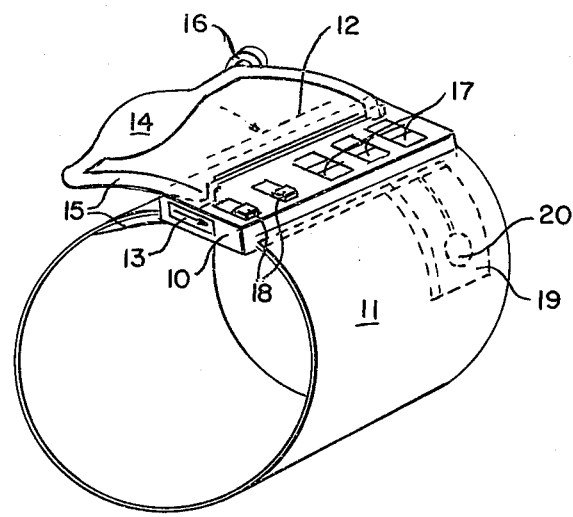
FIG. 1 is a perspective view of a sphygmomanometer of the invention having the buckle and pump at the free end of the cuff.

The buckle 10 of a cuff 11 represented in FIG. 1 extends over the entire width of the cuff band. The buckle 10 is of a more or less parallelepipedal shape. It is equipped with a pliable means 12 represented in broken lines, which is designed to be set and released by laterally mounted slides 13.

It can furthermore be seen in FIG. 1 that all parts of the apparatus are combined, since the buckle 10 of the cuff 11 is the housing for the indicator means 17.

The otherwise necessary long and inconvenient tube leading from the cuff to the manometer for indicating the blood pressure is replaced by a short lead from the cuff 11 to the buckle 10.

A means 14 for the inflation of the cuff is directly mounted to the free end of the cuff by flexible tubes 15. In accordance with the invention it is no longer necessary to work with an inflation pump loosely connected with the cuff, because pump 14, valve 16 and cuff 11 form one unit. This makes the apparatus substantially easier to handle and simpler to operate, because the cumbersome tubes are no longer present.

In electrical sphygmomanometers, the housing contains, in addition to the operating controls 18, a printed circuit for signal processing for the purpose of automatically indicating blood pressure values (systolic and diastolic) through various display units.

If the power supply of the electrical circuit is not provided by a unit such as a generator, for example, connected to pump 14, for example, then a battery or storage battery is housed in the buckle 10.

On the housing of the buckle 10 there is also provided a projection 19 which extends underneath the cuff band and which is represented by broken lines. The projection 19 is provided as the base for a sound pickup 20. It has been found that, when the cuff is attached in the usual manner, the proper sound pickup position of the pickup 20 is not identical with the position of the buckle.

The manufacture of such a cuff becomes simpler also, because a buckle 10 can be made integral with the projection 19, for example by injection molding, and the provision of a separate sound pickup in the sleeve is eliminated.

Figure 2:
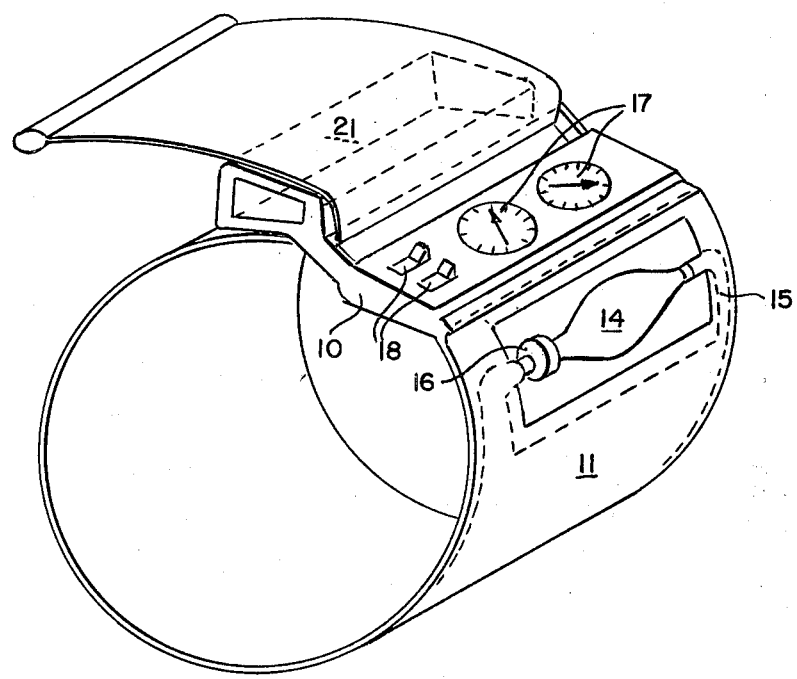
FIG. 2 is a perspective view of a sphygomomanometer of the invention having a buckle provided with an adherent coating to be described below.

In FIG. 2 another version of the new cuff is also represented in perspective. For the same parts the same reference numbers are used in the figure. This is also the case with the readout means, because either analog or digital displays are used in the invention.

Simplifications of design are achieved if the device 14 for pumping up the cuff is set in a cut-out in the cuff, because in this embodiment, too, no long connecting tubes are necessary and a direct connection between the pump 14 and the instruments 17 can be provided within the buckle 10.

The buckle 10 of the cuff represented in FIG. 2 furthermore has the special feature described in copending application Ser. No. 81,733 filed Oct. 4, 1979, namely, that a patch 21 is provided to which a part of the cuff band adheres. The invention is especially suitable for cuffs having such a patch, because their buckles sometimes prove to be somewhat larger than conventional buckles and can easily accommodate the apparatus which they are designed to house.

We claim:

1. In a sphygmomanometer having a microphone, readout means for displaying blood pressure values, a circuit receptive of the signals from the microphone for producing an output applied to the readout means, an inflatable cuff band and means forming a buckle for the cuff band, the improvement wherein: the buckle forming means comprises a housing accommodating the readout means and circuit, means permanently attaching one end of the cuff band to the housing and means defining an elongated slit at least adjacent to the housing through which the free end of the cuff band is received; and the microphone is connected to the cuff band and spaced from the buckle.

2. The sphygmomanometer according to claim 1, wherein the slit defining means comprises means forming the slit in the housing and further comprising means joined to the housing for releasably retaining the free end of the cuff band at a desired position for a user.

3. The sphygmomanometer according to claim 2, further comprising means mounted on the free end of the cuff band for manually inflating the cuff band.

4. The sphygmomanometer according to claim 1, wherein the slit is adjacent the housing and parallel to the end of the housing to which the cuff band is permanently attached and the buckle forming means comprises releasable retaining means for the free end of the cuff band and disposed relative to the housing such that the slit is disposed therebetween.

5. The sphygmomanometer according to claim 4, further comprising means mounted at the permanently attached end of the cuff band for manually inflating the cuff band.--

* * * * *

UNITED STATES PATENT AND TRADEMARK OFFICE
CERTIFICATE OF CORRECTION

PATENT NO. : 4,300,573
DATED : November 17, 1981
INVENTOR(S) : Klaus Rebbe et al It is certified that error appears in the above-identified patent and that said Letters Patent are hereby corrected as shown below:

On The Title Page,
 Assignment, Delete "Clinocon" and insert --Clinicon--.

Signed and Sealed this

Thirty-first Day of August 1982

[SEAL]

Attest:

GERALD J. MOSSINGHOFF

Attesting Officer — Commissioner of Patents and Trademarks